US012016953B2

(12) United States Patent
Larsen et al.

(10) Patent No.: US 12,016,953 B2
(45) Date of Patent: Jun. 25, 2024

(54) METHOD OF PREPARING A GELLING AGENT, THE GELLING AGENT OBTAINED THEREBY, AND THE USE OF SAID GELLING AGENT

(71) Applicant: VIRAMAL LIMITED, Lomdon (GB)

(72) Inventors: Finn Larsen, Hawick (GB); Oliver Bates, Lomdon (GB)

(73) Assignee: Viramal Limited, London (GB)

( * ) Notice: Subject to any disclaimer, the term of this patent is extended or adjusted under 35 U.S.C. 154(b) by 129 days.

(21) Appl. No.: 17/298,266

(22) PCT Filed: Nov. 28, 2019

(86) PCT No.: PCT/EP2019/082893
§ 371 (c)(1),
(2) Date: May 28, 2021

(87) PCT Pub. No.: WO2020/109459
PCT Pub. Date: Jun. 4, 2020

(65) Prior Publication Data
US 2022/0023205 A1      Jan. 27, 2022

(30) Foreign Application Priority Data
Nov. 30, 2018    (EP) .................................... 18209409

(51) Int. Cl.
| | | |
|---|---|---|
| *A61K 9/06* | (2006.01) | |
| *A61K 8/04* | (2006.01) | |
| *A61K 8/73* | (2006.01) | |
| *A61K 8/86* | (2006.01) | |
| *A61K 47/14* | (2017.01) | |
| *A61K 47/32* | (2006.01) | |
| *A61K 47/38* | (2006.01) | |
| *A61Q 19/00* | (2006.01) | |

(52) U.S. Cl.
CPC ................ *A61K 9/06* (2013.01); *A61K 8/042* (2013.01); *A61K 8/731* (2013.01); *A61K 8/86* (2013.01); *A61K 47/14* (2013.01); *A61K 47/32* (2013.01); *A61K 47/38* (2013.01); *A61Q 19/00* (2013.01); *A61K 2800/10* (2013.01); *A61K 2800/5922* (2013.01); *A61K 2800/882* (2013.01)

(58) Field of Classification Search
None
See application file for complete search history.

(56) References Cited

U.S. PATENT DOCUMENTS

| | | | |
|---|---|---|---|
| 4,767,751 A | 8/1988 | Davis | |
| 5,849,019 A | 12/1998 | Yoon | |
| 6,187,323 B1 | 2/2001 | Aiache | |
| 6,579,865 B2 | 6/2003 | Mak | |
| 6,872,382 B1 | 3/2005 | Gamache | |
| 6,967,023 B1 | 11/2005 | Eini | |
| 6,994,863 B2 | 2/2006 | Eini | |
| 7,105,184 B2 | 9/2006 | Pauly | |
| 7,368,122 B1 | 5/2008 | Dow | |
| 8,536,380 B2 | 9/2013 | Scheffler | |
| 8,940,354 B2 | 1/2015 | Marangoni | |
| 9,180,091 B2 | 11/2015 | Bernick | |
| 9,248,136 B2 | 2/2016 | Bernick | |
| 9,289,382 B2 | 3/2016 | Bernick | |
| 2003/0180352 A1 | 9/2003 | Patel | |
| 2004/0143026 A1 | 7/2004 | Shah | |
| 2006/0240111 A1 | 10/2006 | Fernández et al. | |
| 2006/0269485 A1 | 11/2006 | Friedman | |
| 2007/0110812 A1 | 5/2007 | Xia | |
| 2007/0148195 A1 | 6/2007 | Ebert | |
| 2008/0039398 A1 | 2/2008 | Ousler, III | |
| 2010/0137198 A1 | 6/2010 | Eini | |
| 2011/0158920 A1* | 6/2011 | Morley | A61P 17/00 424/59 |
| 2011/0195036 A1 | 8/2011 | Clemente | |
| 2011/0195944 A1 | 8/2011 | Mura | |
| 2012/0301464 A1 | 11/2012 | Friedman | |
| 2014/0161889 A1 | 6/2014 | Mikulásik | |
| 2014/0186278 A1 | 7/2014 | Franke | |
| 2015/0004213 A1 | 1/2015 | Ron | |
| 2015/0283066 A1 | 10/2015 | Katz | |

FOREIGN PATENT DOCUMENTS

| | | |
|---|---|---|
| CA | 3068157 A1 | 12/2018 |
| DE | 102015207621 A1 | 10/2016 |
| EP | 501056 A | 9/1992 |
| EP | 0793996 A1 | 9/1997 |
| EP | 0861657 A2 | 9/1998 |

(Continued)

OTHER PUBLICATIONS

International Search Report and Written Opinion Appl. No. PCT/EP2019/082893, dated Mar. 30, 2020.
Written Opinion of the International Preliminary Examining Authority (IPEA) Appl. No. PCT/EP2019/082893, dated Mar. 4, 2021.
Anonymous, Natural Testosterone; Testosteroids [online]; 2014; downloaded from URL<https://web.archive.org/web/20150114212448/http://www.testosteroids.com/Natural-testosterone>Nov. 21, 2017; 4 pages.
BalanceDocs [online]; 2016; downloaded from <URL http://balancedocs.com/article-library-n-z/testosterone-supplementation/> on Oct. 26, 2018; 4 pages. (Year: 2016).
Boddupalli, Mucoadhesive drug delivery system: An overview, J Adv Pharm Technol Res. 2010, vol. 1(4), p. 381-387.

(Continued)

*Primary Examiner* — Brian Gulledge
(74) *Attorney, Agent, or Firm* — Greenberg Traurig, LLP

(57) ABSTRACT

The present invention relates to a method of obtaining a novel gelling agent. Said method comprises adding ethylcellulose, to a mixture of propyleneglycol laurate and propyleneglycol isostearate at a temperature of between 90° C. and 110° C. The method according to the invention provides a simpler, less energy consuming, cheaper and easier way of obtaining a substantially gelling agent which can be used for manufacturing an oleogel and/or a bigel, for cosmetic and/or pharmaceutical use.

8 Claims, No Drawings

(56) References Cited

FOREIGN PATENT DOCUMENTS

| | | | |
|---|---|---|---|
| EP | 3641821 A2 | 4/2020 | |
| GB | 2581876 A | 2/2020 | |
| JP | H09502724 A | 3/1997 | |
| JP | 11512732 A | 11/1999 | |
| JP | 2000159689 A | 6/2000 | |
| JP | 2005507874 A | 3/2005 | |
| JP | 2007528864 A | 10/2007 | |
| JP | 2010514748 A | 5/2010 | |
| JP | 2010138196 A | 6/2010 | |
| JP | 2012505171 A | 3/2012 | |
| JP | 2013540698 A | 11/2013 | |
| JP | 2014513716 A | 6/2014 | |
| JP | 2020524690 A | 8/2020 | |
| WO | 9320799 A1 | 10/1993 | |
| WO | 1995007699 A1 | 3/1995 | |
| WO | 199620720 A1 | 7/1996 | |
| WO | 9712618 A1 | 4/1997 | |
| WO | 1998032422 A1 | 7/1998 | |
| WO | 9962497 A1 | 12/1999 | |
| WO | 0000120 A1 | 1/2000 | |
| WO | 2003020210 A2 | 3/2003 | |
| WO | 2006082596 A2 | 8/2006 | |
| WO | 2008089405 A1 | 7/2008 | |
| WO | WO2008/081175 A2 | 7/2008 | |
| WO | WO-2008081175 A2 * | 7/2008 | ............ A61K 31/56 |
| WO | 2010040632 A1 | 4/2010 | |
| WO | 2011121604 A2 | 10/2011 | |
| WO | 2012019991 A1 | 2/2012 | |
| WO | 2012156820 A1 | 11/2012 | |
| WO | 2014004018 A1 | 1/2014 | |
| WO | 2014026707 A1 | 2/2014 | |
| WO | 2014193667 A1 | 12/2014 | |
| WO | 2015187840 A2 | 12/2015 | |
| WO | WO2017/120492 A1 | 7/2017 | |
| WO | 2018234871 A2 | 12/2018 | |

OTHER PUBLICATIONS

Drug Label (Physician Information) for Crinone 4% and Crinone 8% (progesterone gel), Jun. 2017.
Drug Label for Striant (testosterone buccal system), Nov. 2009.
Fanchin, Transvaginal Administration of Progesterone, Obstetrics & Gynecology 1997, vol. 90(3), p. 396-401.
Germond, Comparison of the efficacy and safety of two formulations of micronized progesterone (Ellios™ and Utrogestan™) used as luteal phase support after in vitro fertilization, Fertility & Sterility 2002, vol. 77, No. 2, p. 313-317.
Kumar, Denture Adhesives in Prosthodontics: An Overview, J Int Oral Health 2015, vol. 7, Suppl 1, p. 93-95.
Nahoul, Profiles of plasma estrogens, progesterone and their metabolites after oral or vaginal administration of estradiol or progesterone, Maturitas 1993, vol. 16, p. 185-202.
New Dictionary of Traditional Chinese Medicine, Wang Benxiang, Tianjin Science and Technology Press, pp. 840 published on May 31, 1996 (English translation).
PCT/IB2019/059105 International Search Report and Written Opinion dated Jan. 8, 2020.
PCT/US2017/012564 International Search Report and Written Opinion dated Apr. 18, 2017.
Peppas, Hydrogels as mucoadhesive and bioadhesive materials: a review, Biomaterials 1996, vol. 17(16), p. 1553-1561.
Progesterone Dosage Guide from Drugs.Com website, printed Oct. 7, 2018.
Russo, A focus on mucoadhesive polymers and their application in buccal dosage forms Journal of Drug Delivery Science & Technology 2016, vol. 32, p. 113-125.
Shaikh, Mucoadhesive drug delivery systems, J Pharm Bioallied Sci. 2011, vol. 3(1), p. 89-100.
Simon, The absorption of oral micronized progesterone: the effect of food, dose proportionality, and comparison with intramuscular progesterone, Fertility & Sterility 1993, vol. 60, No. 1, p. 26-33.
Singh et al., Preparation and characterization of novel carbopol based bigels for topical delivery of metronidazole for the treatment of bacterial vaginosis. Materials Science and Engineering C. vol. 44. pp. 151-158. Aug. 5, 2014.
Sudhakar, Buccal bioadhesive drug delivery—A promising option for orally less efficient drugs, Journal of Controlled Release 2006, vol. 114, p. 15-40.
Wu et al., "Determination of danazol in human plasma by liquid chromatogram-mass spectrometry", Clin Pharm J, 2005, vol. 40, No. 10, 3 pages.
Zhu, The development of polycarbophil as a bioadhesive material in pharmacy, Asian Jounral Pharmaceutical Science, 2013, p. 218-227.
Bucala et al. Formation of covalent adducts between cortisol and 16 alpha-hydroxyestrone and protein: possible role in the pathogenesis of cortisol toxicity and systemic lupus erythematosus. Proceedings of the National Academy of Sciences of the United States of America, 1982, 79(10), pp. 3320-3324.
Cuervo et al. Searching for Alternative Danazol Metabolites Through Accurate Mass with LC/MS Q-TOF. Agilent Technologies, 2015, pp. 1-6.
Danazol, Cayman Chemical. Product Information: Nov. 16, 2022.
Drug Delivery System, 2009, vol. 24-4, pp. 384-393.
Gounden et al., LC-MS/MS detection of increased androstenedione levels in patients receiving danazol therapy. Therapeutic drug monitoring, 2014, 36(6), pp. 828-829.
Marcoux et al., Laparoscopic Surgery in Inferile Women with Minimal or Mild Endometriosis, New England Journal of Medicine, 1997, vol. 337, No. 4, pp. 217-222.
O'Sullivan et al. Edible oleogels for the oral delivery of lipid soluble molecules: Composition and structural design considerations. Nov. 2016. Trends in Food Science & Technology. vol. 57, Part A, pp. 59-73.
PubChem. Danazol. Retrieved Oct. 20, 2022 <https://pubchem.ncbi.nlm.nih.gov/compound/Danazol>.

* cited by examiner

METHOD OF PREPARING A GELLING AGENT, THE GELLING AGENT OBTAINED THEREBY, AND THE USE OF SAID GELLING AGENT

This application is a 371 filing of International Patent Application PCT/EP2019/082893 filed Nov. 28, 2019, which claims priority to European patent application no. 18209409.4 filed Nov. 30, 2018.

TECHNICAL FIELD

The present invention relates to a method for preparing a gelling agent, the gelling agent obtained thereby, and the use of said gelling agent for preparing an oleogel and/or a stable bigel.

BACKGROUND OF THE INVENTION

Administration of an active pharmaceutical ingredient (API) to an individual requires careful consideration and planning both to optimise delivery of the API and to minimizing potential adverse side effects. For instance, when an API is applied to the skin, it is desirable to achieve good penetration of the API into the skin layers. The formulation used to 'carry' the API is often referred to as a vehicle, and since penetration of the API into the skin mainly occurs by passive diffusion through the stratum corneum the vehicle must be arranged for providing good penetration abilities.

The choice of vehicle will depend upon the nature of the API, the site of treatment, as well as the preferences of the patient. For instance, some API's are hydrophilic i.e. they are preferably delivered in a hydrophilic vehicle, e.g. a hydrogel. However, even though hydrogels have good patient compliance, a major problem with hydrogels is that they can only carry hydrophilic active ingredients. Furthermore, since they are hydrophilic they have limited access to penetration across the skin. In contrast, oleogels which are the best carriers for lipophilic APIs, are oleaginous in nature and will accordingly provide a greasy feeling e.g. by leaving a greasy residue on the skin, which results in low patient compliance, especially for dermatological and cosmetic applications.

Thus, APIs and/or or cosmetic ingredients have conventionally been delivered to the skin in emulsions (oil-in-water or water-in-oil) e.g. in the form of creams, ointments, gels, pastes, and lotions, thereby obtaining the benefits of both the oil and water phase, e.g. good penetration of the API over the skin barrier. However, emulsions are known to destabilise over time, e.g. showing phase separation. In order to prevent this effect, the emulsions are stabilised by the incorporation of emulsifiers, surfactants, and the like during their preparation. However, such stabilisation compounds are known to cause skin irritation, and incorporation of such compounds are obviously not desirable.

In order to overcome said problems, bigels are gaining more attention and are increasingly become more important in the food, pharmaceutical and cosmetic industry. A bigel is a uniform semisolid dispersion system that visually appear as a single gel, but in which an oleogel and an aqueous gel, are mixed together e.g. by applying a high shear rate. Bigels are not emulsions, and one of the major advantages of bigels is the improved stability compared to emulsions (water-in-oil and oil-in-water), emulgels, hydrogels and oleogels, which makes bigels a potent vehicle for API's and/or for cosmetic ingredients. The enhanced physicochemical stability of the bigels can be attributed to the formation of extra fine colloidal dispersions, which is due to the immobilization of one gel (e.g. the oleogel) in a three-dimension gel network of the other gel (e.g. the aqueous gel). On storage at room temperature, the two components of the bigel do not get separated and the bigel therefore remains stable.

Further, no separation of the aqueous gel and oleogel is detected when a bigel is applied to the skin. Thus, by converting oleogels and hydrogels into bigels, a good patient compliance is provided without compromising the beneficial effects of the individual water and oil phases, as such bigels may comprise both hydrophilic and hydrophobic APIs and/or cosmetic ingredients. It has further been shown that the amalgamation of two gels may possess synergistic effect, resulting in improve drug permeation over the skin, due to the presences of both hydrophilic and lipophilic properties, i.e. the ingredient(s) in a bigel may penetrate though the skin easier, and the bigels are therefore starting to become the choice for topical and/or transdermal drug delivery. Another benefit of the bigels is that they possess electrical conductivity, which makes them a suitable carrier for iontophoretic drug delivery.

A bigel is normally obtained by preparing the hydrogels and oleogels individually, after which the two gels are mixed together e.g. by applying a high shear rate. Examples of methods for formulating such bigels are e.g. disclosed in EP1083880 and EP2120865.

As is evident from said publications the bigel is prepared by the following steps:
 providing an oleogel comprising at least one oil-composition gelled with at least one cellulose polymer;
 providing an aqueous gel; and
 mixing the oleogel and the aqueous gel together to form a bigel.

The cellulose polymer used as a gelling agent may e.g. be chosen from ethylcellulose, non-sodium carboxy methylcellulose, and mixtures thereof. However, one preferred gelling agent in EP2120865 is the formulation Emulfree® P, obtainable from Gattefosse. Said compound contains ethylcellulose, propylene glycol isostearate and propylene glycol laurate in relative proportions of 8:2:90% by weight (wt %), respectively, and is obtained by mixing the three components in a single step.

However, one of the main problems with the manufacturing of the Emulfree® P, as well as other compositions in which ethylcellulose are used for gelling an oil-composition, is that said composition has to be heated above the glass transition temperature of the ethylcellulose, approximately 130-150° C. in order for the ethylcellulose to dissolve in the oil-composition, e.g. propylene glycol isostearate and propylene glycol laurate. Said method therefore not only requires a high energy consumption but are accordingly also extremely expensive.

A further problem is that the Emulfree® P is yellow, and has a characteristic odour, physiochemical parameters which may be transferred to the resulting oleogel and consequently to the bigel, and which may impose unwanted effects on the final products, effects which in some situations have to be masked with e.g. fragrances and/or pigmentations in order to improve patient compliance.

SUMMARY OF THE INVENTION

Thus, the inventors of the present invention has found that an improved gelling agent for manufacturing oleogels and/or bigels is required.

It is accordingly a first aspect of the present invention to provide a novel method of manufacturing a gelling agent for providing an oleogel and consequently for providing a stable bigel comprising said oleogel, it is a second aspect of the present invention to provide a novel method of manufacturing a gelling agent in a simpler, and more energy efficient way than hitherto known.

it is a third aspect of the present invention to provide an improved gelling agent for productions of oleogels and/or stable bigels, and it is a fourth aspect of the present invention to provide a gelling agent having gelling characteristics corresponding to Emulfree® P, but with a less significant color and/or odor.

These and further aspect are achieved according to the present invention by providing a method for manufacturing a gelling agent, said method comprises the following consecutive steps:

a) mixing propyleneglycol laurate and propyleneglycol isostearate, providing a first mixture,
b) adding ethylcellulose to the first mixture under stirring, thereby providing a second mixture, and
c) continuously stirring the second mixture until a substantially homogeneous gelling agent is formed, and wherein step a), b) and c) are performed at a temperature between 90° C. and 110° C.

DETAILED DESCRIPTION OF SPECIFIC EMBODIMENTS

Ethylcellulose is a well known polymer capable of structuring oils (oil-compositions) into solid gel networks, i.e. providing an oleogel. It is presently the only direct food-grade polymer gelling agent, and said polymer is therefore an obvious candidate also for preparation of vehicles for topical and/or transdermal delivery.

Ethylcellulose is a semi-crystalline cellulose polymer derivative, consisting of a cellulose backbone with ethoxyl substitutions at hydroxyl groups, and undergoes a thermoreversible sol-gel transition in the presence of liquid oil. This unique behaviour is based on the polymer's ability to associate through physical bonds.

However, in order for ethylcellulose to function as a gelling agent, the ethylcellulose-oil mixture must be heated above the glass transition temperature of the ethylcellulose, approximately 130-150° C. (dependent on the molecular weight of the ethylcellulose), at which point the ethylcellulose will dissolve fully in the oil. Dissolution of ethylcellulose into the oil above this glass transition temperature takes place due to the melting of the glassy regions of the polymer melt, resulting in exposure of the ethoxy groups to the solvent.

However, the inventors of the present invention have found that a stable and a substantially homogeneous gelling agent, comprising ethylcellulose, can be obtained at temperatures well below the glass transition temperature of the ethylcellulose, by using the method according to the invention. The inventors have surprisingly found that the ethylcellulose, contrary to the expectations, will be incorporated into a mixture of propyleneglycol laurate and propyleneglycol isostearate when the ethyl cellulose is added to said mixture at a temperature of between 90° C. and 110° C., preferably about 100° C. The method according to the invention therefore provides a simpler, less energy consuming, cheaper and easier way of obtaining a substantially homogeneous gelling agent. Said gelling agent is preferably cooled to e.g. room temperature i.e. about 20° C., before said gelling agent is used for preparing an oleogel e.g. for use in preparing a bigel.

The method according to the inventing can be conducted in ambient air, and it is accordingly not necessary that said method is performed in a protected atmosphere, consisting e.g. of $N_2$.

In addition, the inventors of the present invention have found, that the method according to the invention provides a liquid/viscous gelling agent having a more transparent and clearer appearance with a less characteristic odour when compared to the known Emulfree® P. Thereby the gelling agent obtained by said method, will increase consumer acceptability when said gelling agent is used for manufacturing an oleogel and/or a bigel, e.g. for pharmaceutical and/or cosmetic use.

The compounds propyleneglycol laurate and propyleneglycol isostearate are well known emollients, i.e. said compounds have the quality of softening and/or soothing the skin. However, the inventors of the present invention have also found that in addition to the softening/soothing properties obtained by having said emollients in an oleogel manufactured using the gelling agent according to the invention, the combination of ethylcellulose with said emollients provides a synergistic effect which aids in enhancing the permeation/penetration of an ingredient (e.g. an API or cosmetic ingredient) in an oleogel and/or bigel, across the skin, thereby improving the benefits of the gelling agent according to the invention.

In a preferred embodiment the ethylcellulose is added step-wise to the first mixture, i.e. the entire content of the ethylcellulose is neither added at the same time nor continuously to the first mixture, but smaller amounts of ethylcellulose, e.g. between ⅒ to about ⅓ of the total amount of ethylcellulose, are added to the first mixture in a series of distinct stages, as the inventors of the present invention has found that such an addition aids is obtaining a substantial homogeneous gelling agent, and/or that less mixing is required in step c).

It is preferred that the method according to the invention is performed under a constant stirring, e.g. at a rotational speed of at least 800 rpm, preferably at least 1000 rpm. However, the rotating speed may be varied, e.g. by also adjusting the mixing/stirring period, since the only requirement being, that a homogeneous gelling agent is formed.

Many ethylcellulose products are commercially available and are differentiated according to the viscosity in centipoise (cP) of the solution that they will create when dispersed in 80% toluene and 20% ethanol. Commonly used ethylcellulose ranges from, 10, 20 or 45 cP, which is based on the average molecular weight of polymers present, where a higher molecular weight corresponds to a greater viscosity. However, in the present invention it is preferred to use an ethylcellulose having an average molecular weight of about 160,000 g/mol, and/or an ethoxyl substitution degree of between 48.0-49.5%, as the use of such an ethylcellulose has proven beneficial in obtaining a gelling agent having the desired characteristics.

The inventors of the present invention have further found that in order to ensure that the gelling agent obtained by the method according to the invention can be used for preparing an oleogel and/or a bigel e.g. for pharmaceutical and/or cosmetic use, i.e. a bigel which easily can be applied to the skin, adheres firmly to the skin (even after washing), and does not leave a greasy or messy feeling on the skin, it is preferred that the gelling agent has a viscosity between 400 and 500 mPa·s, measured using a VRM-08 LAMY viscosimeter equipped with a MS DIN 1-2 module at a shear rate of 17.73 $s^{-1}$ and at 46° C.

Such a viscosity will further ensure that the gelling agent according to the invention easily can be mixed/added/poured into at least one oil-composition (a composition comprising one or more oil-compound(s)) in order to prepare the oleogel, but without negatively affecting the gelling agent's ability to be incorporated in the oil-composition and accordingly prepare the desired oleogel.

The inventors of the present invention have also found that such a viscosity is obtained when the amount of ethylcellulose added in step b) is at least 4 wt % (% by weight) and not more than 5 wt %, based on the total weight of the gelling agent. Preferably the amount of ethylcellulose added in step b) is about 4.5 wt %, about 4.75 wt %, or about 5 wt %, based on the total weight of the gelling agent.

It is further preferred that the amount of propyleneglycol laurate added in step a) is at least 70 wt % and not more than 90 wt %, based on the total weight of the gelling agent, and that the amount of propyleneglycol isostearate added in step a) is at least 5 wt % and not more than 25 wt %, based on the total weight of the gelling agent.

If the gelling agent contains 5 wt % ethylcellulose, it is preferred that the amount of propyleneglycol laurate and propyleneglycol isostearate is adjusted accordingly, such that the final gelling agent contains about 25 wt % propyleneglycol isostearate and about 70 wt % propyleneglycol laurate, i.e. the % ratio of the weight (wt %-ratio) of ethylcellulose, propylene glycol isostearate and propylene glycol laurate in the gelling agent is respectively 5:25:70.

In an alternative embodiment the wt %-ratio of ethylcellulose, propylene glycol isostearate and propylene glycol laurate are 4.5:5.5:90. It is however preferred that the gelling agent according to the invention has a wt %-ratio of ethylcellulose, propylene glycol isostearate and propylene glycol laurate respectively of 4.75:5.25:90.

The gelling agents obtained using such ratios will all have characteristics corresponding to the known Emulfree® P obtainable from Gatteforse (France), i.e. they have a corresponding viscosity, corresponding pH-value, and a corresponding density, and said gelling agents are all capable of providing oleogels and/or bigels with similar viscosities as the Emulfree® P. However, the oleogels prepared using the gelling agent according to the invention will have an improved odour and transparency, and even though they have the same viscosities as oleogels prepared using Emulfreee® P, less ethylcellulose was needed in order to obtain said oleogels, and said oleogels are accordingly cheaper to manufacture.

The gelling agent obtained using the method according to the invention, is preferably used for preparing an oleogel.

Said oleogel may be used directly, e.g. as a vehicle for delivering an API or a cosmetic ingredient, but may also be used in the preparation of a bigel, e.g. via the following steps:
   providing an oleogel comprising at least one oil-composition gelled with the gelling agent according to the invention;
   providing an aqueous gel; and
   mixing the oleogel and the aqueous gel together to form a stable bigel.

The bigel is preferably prepared as disclosed in either EP1083880 or EP2120865, the main difference being that the gelling agent used for preparing the oleogel is the gelling agent obtained by the method according to the invention, preferably having one of the preferred wt % ratios disclosed above.

In order to prepare the oleogel, one or more oil-compositions are gelled using the gelling agent according to the invention, e.g. by added the gelling agent to the oil-composition(s) under stirring.

The oil-composition(s) used for preparing the oleogel may be the same as disclosed in EP1083880 and/or EP2120865, and is preferably selected from mono-, di-, and triglycerides of synthetic, semi-synthetic and natural origin, and mixtures thereof, e.g. a mixture of capric/caprylic triglycerides.

In order to prepare the aqueous gel, it is preferred that said gel comprises at least one component whose viscosity may be adjusted e.g. by changing the pH, ion content, temperature etc. of the aqueous gel. In one embodiment, the viscosity is adjusting by the use of thickening agents whose viscosity may be adjusted by factors such as changing the salt or ion concentration. It is however preferred that the composition for preparing the aqueous gel comprises at least one component whose viscosity is pH dependent, such that said component act as gelling agents when the pH is suitably adjusted. A suitable component is sodium carboxymethylcellulose but in a preferred embodiment the composition for preparing the aqueous gel comprises one or more carbomers.

Carbomer is a generic name for a family of polymers known as carbopols which are homopolymers of acrylic acid, cross-linked with an allyl ether of pentaerythritol, an allyl ether of sucrose, or an allyl ether of propylene. As a group, they are dry powders with high bulk densities, and form acidic aqueous solutions (pH around 3.0), which thicken at higher pHs (around 5 or 6). They swell in aqueous solution of that pH as much as 1000 times their original volume, and the viscosity of the aqueous gel can therefore be adjusted by adjusting the concentration of the carbomer in the aqueous gel and the pH-value of said gel. Preferred examples of such carbomers are Carbopol 974 and Carbopol 980 NF.

Typically, the component whose viscosity is pH dependent is present in the aqueous gel in a proportion of between about 3 and about 30% wt % of the aqueous gel, preferably between 5 and 25%, or between around 8% and 12%, e.g. about 9 wt % based on the total weight of the aqueous gel, depending upon the desired viscosity and other properties of the bigel to be produced.

The inventors of the present invention have shown that, if the aqueous gel is too viscous or is not viscous enough, it may be difficult to incorporate the oleogel properly into the aqueous gel when the two gels are mixed together. In other words, there is an optimum viscosity range for the aqueous gel at the stage when it is mixed together with the oleogel. Preferred viscosities of the aqueous gel, prior to mixing with the oleogel, lies between about 100 and about 1,000 mPa·s (cP), measured using a Lamy RM-08 with an MS Din 1.9 module at 23° C. under a shear stress of $0.8\ s^{-1}$.

If the viscosity of the aqueous gel lies outside said range, the viscosity of the aqueous gel may preferably be adjusted before being mixed with the oleogel. This may in one embodiment be obtained by heating the aqueous gel, e.g. to a temperature below 50° C., however other suitable ways for adjusting the viscosity is also contemplated within the scope of the present invention.

The inventors have not been able to identify a preferred viscosity range for the oleogel. The only requirement for the viscosity of the oleogel, is that the oleogel easily can be mixed with the aqueous gel, i.e. it is preferably neither to thick nor to thin. In one embodiment the viscosity of the oleogel corresponds to the viscosity of the aqueous gel. If desired the viscosity of the oleogel can be lowered by heating the oleogel e.g. to a temperature below 50° C.

The step of mixing the oleogel and aqueous gel together typically comprises incorporating the oleogel into the aqueous gel until a mixture of substantially uniform appearance is obtained. Alternatively, the aqueous gel may be incorporated into the oleogel until a homogenous mixture of substantially uniform appearance is obtained.

As mentioned above, the inventors have realised that the viscosity of the aqueous gel preferably is in a certain range in order to obtain an optimal mixing of the two gels, especially when they are mixed together on a large scale. However, this may result in a bigel having a viscosity which is not desirable for the indented purpose. It is in such situation preferred that the aqueous gel compromises a component whose viscosity may be adjusted by changing the pH-value, as it then will be possible to change the viscosity of the entire bigel by adjust the pH-value after the bigel has been formed. It is accordingly preferred that method according to the invention comprises a pH-adjusting step, wherein one or more pH adjusting agents are added to the bigel, i.e. after the aqueous gel and the oleogel are mixed together. Furthermore, mixing the oleogel and the aqueous gel with a lower viscosity, ensures that said two gels may be mixed easier, after which the pH-adjusting step will provide the resulting bigel with the optimal/desired viscosity.

Preferably, said pH-adjusting step comprises adding at least one pH adjusting agent to the bigel, in an amount between 0.01 wt % and 1 wt % based on the total weight of the bigel. The pH-adjusting agent may be any compound/composition capable of adjusting the pH-value in the bigel, e.g. sodium hydroxide (if a higher pH-value is desired) or sorbic acid (if a lower pH value is desired).

In a preferred embodiment the pH-adjusting step is conducted under vacuum to prevent the incorporation of air into the product, and/or may preferably be conducted as one, two, three or more distinct stages. For instance, in a first pH-adjusting step a sodium methylparaben solution may be added to the bigel, and in a second pH-adjusting step, a sodium hydroxide solution may be added to the bigel.

Thus, a person skilled in the art person can easily obtain a bigel with the desired viscosity, e.g. by using suitable concentrations of one or more of the following; gelling agent, the component whose viscosity may be adjusted by changing the pH-value, and the pH-adjusting agent.

The optimal viscosity depends on the intended use of the bigel. For instance, "shower gels" typically have a viscosity within the range 1,000-20,000 cP (1-20 Pa·s), lotions typically have a viscosity within the range 1,000-30,000 cP (1-30 Pa·s), while creams and ointments have a higher viscosity above 30,000 cP (30 Pa·s), preferably above 80,000 cP (80 Pa·s). Suitable creams or ointments typically have a viscosity within the range of 30,000-150,000 cP (30-150 Pa·s), and more preferably between 80,000-140,000 cP (80-140 Pa·s) or 90,000-120,000 cP (90-120 Pa·s). All viscosities are measured using a Lamy VRM-08 viscometer using an appropriate MS DIN module at a temperature of 23° C. and at a shear stress of 0.8 $s^{-1}$.

A person skilled in the art will understand that it is not always necessary to measure the viscosity of the bigel in order to obtain a bigel with the desired viscosity. It can also be determined by feel whether a bigel has a viscosity suitable for use as a lotion, cream or ointment. In addition, once the components and conditions for making a bigel having a desired viscosity have been determined, it is possible to recreate a bigel having that specific viscosity by following the same procedures.

For a bigel formulation intended for human topical and/or transdermal use, the pH-adjustment step may be a neutralisation step, i.e. aiming at bringing the pH-value of the bigel towards pH 7. A person skilled in the art will understand that it is not required that a pH-value of 7 is obtained in the bigel, only that the pH obtains a pH-value where it will not harm and/or irritate the epidermis/skin at the treatment site.

When the bigel obtained according to the method of the present invention is intended for use as a pharmaceutical composition, the bigel may comprise at least one active pharmaceutical ingredient (API), and when the bigel is intended for cosmetic purposes, said bigel may comprise none, one or more active cosmetic ingredients. The active ingredients (pharmaceutical and/or cosmetic) can be added to either or both of the oleogel and the aqueous gel.

For certain intended uses, in particular for the purpose of a topical administration, the bigel can comprise the same active ingredient in both the oleogel and the aqueous gel. This is advantageously since the inventors have found that the release profile of the active ingredient into the skin from such a bigel, is considerably better than that obtained with a composition based on only one type of gel, oily or aqueous. (Comparisons have been made for a given volume of composition applied and a given concentration of active ingredient relative to the total weight of the composition). This is particularly advantageous when using the bigel as an active ingredient reservoir in a transdermal release system. On the skin, the active ingredient(s) dissolved in the aqueous gel is rapidly taken up by the epidermal layers, which allows the percutaneous passage to start quickly. The active ingredient(s) in the oleogel must first, as a function of its oil/water partition coefficient, pass into the aqueous gel in order to pass into the epidermal layers: this fraction in the oleogel will thus be released with a greater delay, after the active ingredient(s) dissolved in the aqueous gel has been released.

In some situations the active ingredients to be incorporated into the bigel have the best solubility in an alcohol. And in order to ensure that such ingredients also can be delivered using a bigel as the vehicle, an alcohol solvent may be added and/or incorporated into the oleogel, preferably in step b), i.e. before the oleogel is mixed with the aqueous gel. The alcohol is preferably a C1-C6 alcohol, preferably ethanol, and is added to and/or incorporated in the oleogel in an amount between 0 wt % and 7% wt % based on the total weight of the bigel, preferably about 3.5 wt %.

Suitable ingredients that may be included in a bigel for pharmaceutical and/or cosmetic use may be any desirable active ingredient, e.g. hormones; corticoid and corticoid derivatives; dermatological active ingredients; antimicrobial agents; anti-inflammatory agents and wound repair agents.

In a preferred embodiment the bigel comprises a hormone selected from oestradiol (or other oestrogen), progesterone (or progestins) and testosterone, and said hormone is preferably present in the bigel at between 0.5 and 2.5 wt % or even more, and more preferably between 0.5 and 1.5 wt %, relative to the total weight of the bigel. In a preferred embodiment, the bigel comprises 1 wt % hormone.

The ratio of the weight of oleogel to the weight of aqueous gel may be between about 10:90 and about 90:10, preferably between 30:70 and 70:30, and more preferably between 40:60 and 60:40. The actual ratio chosen typically depends upon the active ingredients(s) present in each gel, particularly since it is appreciated that there is a higher bioavailability from the aqueous gel, as well as upon the desired physical characteristics of the bigel to be achieved. For example, the higher the percentage of oil, the higher the oily feel to the bigel.

The bigel may further comprise one or more standard ingredients for gels, creams and ointments, including texture agents, antioxidants, dyes/colouring agents, preservatives or fragrances. Said ingredients may be added to the oleogel or the aqueous gel before mixing or added to the bigel after the two gels have been combined.

EXPERIMENTS

Experiment A: Manufacturing a Gelling Agent

In order to find the optimal gelling agent, a number of samples with different ratio of the weight (wt %-ratios) of ethylcellulose, propylene glycol isostearate and propylene glycol laurate were manufactured, and compared to Emulfree® P, obtained from Gattefosse.

Ten gelling agent samples having different wt %-ratios of ethylcellulose, propylene glycol isostearate and propylene glycol laurate were manufactured according to the present invention.

Said ten compositions were manufactured as follows:
propyleneglycol laurate (Lauroglycol FCC obtained from Gattefosse) and propyleneglycol isostearate (Hydrophilol isostéarique obtained from Gattefosse) were mixed together in a reaction container placed on a magnetic stirrer (IKA® RCT) set at 1000 rpm, and at a temperature of 100° C., thereby providing a first mixture,
the ethylcellulose (ethylcellulose N50 manufactured by Aqualon/Hercules) were divided in three portions and step-wise added to the first mixture under continuous stirring at 1000 rpm, and at a temperature of 100° C., thereby providing a second mixture, and
said second mixture were stirred at constant stirring at 1000 rpm, and at a temperature of 100° C. until a substantially homogeneous gelling agent was formed (this took about 15 minutes).

The gelling agents were allowed to cool to room temperature before being used for further testing.

After the ten gelling agent samples were manufactured, the following parameters were tested for each sample, and for the conventional Emulfree® P composition.

Appearance

The visual appearance and odor assessment were performed by human subjects in laboratory settings.

Density:

Density was assessed by determining the mass of the sample contained in a given volume of a 6 ml stainless steel thimble at room temperature, pH-value:

pH was measured using a WTW 340i set pH-meter.

Viscosity:

Viscosity was measured using a VRM-08 LAMY viscosimeter equipped with a MS DIN 1-2 module. The speed was fixed at 50 rpm (share rate of 17.73 $s^{-1}$) and the temperature was fixed at 46° C. Time: up to stabilization.

Results:

The results from are compiled in table 1 and 2.

TABLE 1

| Batch no | F02U219 | F03U221 | F04U222 | F05U223 | F06U225 | Emulfree ®P |
|---|---|---|---|---|---|---|
| Ethylcellulose Concentration | 2% | 4% | 6% | 8% | 5% | / |
| Propyleneglycol isostearate | 8% | 6% | 4% | 2% | 5% | / |
| Propyleneglycol laurate | 90% | 90% | 90% | 90% | 90% | / |
| Organoleptic characters | transparent liquid with a slight odour | transparent liquid with a slight odour | transparent liquid with a slight odour | transparent liquid with a slight odour | transparent liquid with a slight odour | transparent yellow liquid with characteristic odour |
| Viscosity mPa · s | 51 | 146 | 652 | 2869 | 600 | 493 |
| Density | 0.93 | 0.92 | 0.92 | 0.92 | 0.92 | 0.93 |
| pH | 6.13 | 6.14 | 6.28 | 6.29 | 6.25 | 6.37 |

TABLE 2

| Batch no | F07U226 | F08U227 | F09U228 | F13U243 | F16U248 | Emulfree ® P |
|---|---|---|---|---|---|---|
| Ethylcellulose Concentration | 4.5% | 4.5% | 4.50% | 5% | 4.75% | / |
| Propyleneglycol isostearate | 5.5% | 23.9% | 47.75% | 25% | 5.25% | / |
| Propyleneglycol laurate | 90% | 71.6% | 47.75% | 70% | 90% | / |
| Organoleptic characters | transparent liquid with a slight odour | transparent yellowish liquid with a slight odour | transparent yellowish liquid with a slight odour | transparent yellowish liquid with a slight odour | transparent yellowish liquid with a slight odour | transparent yellow liquid with characteristic odour |
| Viscosity mPa · s | 420 | 352 | 369 | 463 | 446 | 493 |
| Density | 0.93 | 0.92 | 0.91 | 0.91 | 0.92 | 0.93 |
| pH | 6.20 | 6.45 | 6.58 | 7.05 | 6.67 | 6.37 |

As is evident from table 1 and 2, the three compositions F07U226, F13U243 and F16U248 had characteristics, i.e. viscosities, pH-value and density, resembling the conventional Emmulfree® P formulation.

The conventional Emulfree® composition contains ethylcellulose, propylene glycol isostearate and propylene glycol laurate in a relative proportion of 8:2:90 wt %, respectively.

However, when a composition (batch F05U223 in table 1) having an identical wt % ratio of ethylcellulose, propylene glycol isostearate and propylene glycol laurate as Emulfree® P (i.e. 8:2:90 wt %), was manufactured according to the present invention, the obtained viscosity was so high (2869 mPa·s) that said sample could not be used as a gelling agent for preparing an oleogel and/or bigel according to the invention.

The inventors of the present invention found that by first mixing propyleneglycol laurate and propyleneglycol isostearate and thereafter adding ethylcellulose to the thereby obtained solution, a temperature well below the glass transition temperature of the ethylcellulose (of about 130-150 C) could be used, instead of as conventionally having to heat the entire mixture to a temperature at or above said glass transition temperature in order to ensure that the ethylcellulose was fully dissolved.

Different temperatures were tested, but the best results for providing a substantially homogeneous gelling agent was obtained in the temperature range between 90° C. and 110° C., preferably about 100° C. At temperatures below 80° C., a homogenous composition was not provided.

Experiment B: Manufacturing a Bigel

In order to evaluate which of the three sample gelling agents F07U226, F13U243 and F16U248 had characteristics resembling the conventional Emulfree® P formulation, 200 g bigels were manufactured using each sample gelling agent and Emulfree® P. Said bigels were manufactured as follows (all wt % are based on the final bigel):

An aqueous gel was prepared by heating 65.45 wt % purified water to 50° C., and then dissolving 0.10 wt % sorbic acid in said water under stirring at 3000 rpm for 10 minutes using a SYLVERSON® type mixer. The thereby obtain mixture, were cooled to 25° C., and 1.40 wt % Carbomer CARBOPOL® 980 NF was dispersed in said mixture under stirring from 2000 to 6000 rpm using a SYLVERSON® type mixer, thereby providing the aqueous gel.

The oleogel was prepared by dissolving 3.50 wt % ethanol (96.5%) in 21 wt % Caprylic/Capric triglycerides LABRAFAC CC® under stirring for 5 minutes, using a magnet stirrer. Thereafter, 4 wt % Emulfree® or 4 wt % of respective three sample gelling agents, was added to the mixture under stirring for 10 minutes using a magnet stirrer, thereby creating an oleogel.

Thereafter, the oleogel was added to the aqueous gel under quick stirring using an ULTRA TURRAX® type mixer at 13500 rpm for 10 minutes, and the thereby obtained first composition was transferred to a mortar.

In order to adjust the pH-value of the bigel, two pH-adjusting solutions, Sol A and Sol B, were prepared.

Sol A: 0.25 wt % Sodium methylparaben was dissolved in 3.30 wt % purified water under magnetic stirring.

Sol B: 0.20 wt % sodium hydroxide was dissolved in 1.80 wt % purified water under magnetic stirring.

In order to pH-adjust (neutralize) the bigel; Sol A was first added to the bigel under mixing, and then Sol B was added under mixing.

The characteristics of the thereby obtained bigels are evident from table 3 below.

TABLE 3

| Gelling agent | | Bigels | | |
| --- | --- | --- | --- | --- |
| Batch no | Composition | Batch no | Visual aspect | Viscosity* mPas |
| Emulfree P | / | F06T165 | White bigel (cream) | Around 125000 |
| F07U226 | EC 4.5% PGI 5.5% PGL 90.0% | F10U236 | White bigel (cream) | Around 115000 |
| F13U243 | EC 5% PGI 25% PGL 70% | F14U245 | White bigel (cream) | Around 120000 |
| F16U248 | EC 4.75% PGI 5.25% PGL 90.00% | F17U249 | White bigel (cream) | Around 120000 |

EC: Ethylcellulose;
PGI: Propyleneglycol Isostearate;
PGL: Propyleneglycol Laurate The viscosity was measured using a VRM-08 LAMY viscosimeter equipped with a MS DIN 1.3 module. The speed was fixed at 5 rpm (shear rate of 0.8 s$^{-1}$) and the temperature was fixed at 23° C. Time: 10 s & 30 s.

Based upon the obtained results the gelling agent with batch no. F16U248 was selected for further testing, however the other two sample gelling agents, batch no. F07U226, and F13U243, were also considered suitable gelling agents.

Experiment C: Manufacturing a Bigel Containing 1 wt % Testosterone

In order to evaluate if the bigel created using the sample gelling agent according to the invention, could be used as a suitable vehicle for delivering an API, a bigel containing 1 wt % testosterone, and manufactured using the gelling agent according to the invention (batch F16U248), was compared to a similar bigel manufactured using the conventional Emulfree® P composition.

The respective bigels were manufactured as follows (all wt % are based on the final bigel):

An aqueous gel was prepared by first heating 65.45 wt % purified water to 50° C., and then dissolving 0.10 wt % sorbic acid in said water, under stirring at 3000 rpm for 10 minutes using a SYLVERSON® type mixer. The thereby obtain mixture was then cooled to 25° C., hereafter 1.40 wt % Carbomer CARBOPOL® 980 NF was dispersed in said mixture under stirring from 2000 to 6000 rpm using a SYLVERSON® type mixer, thereby providing the aqueous gel.

The oleogel was prepared by dispersing 1 wt % testosterone in 20 wt % Caprylic/Capric triglycerides LABRAFAC CC® under stirring at 8000 rpm using an ULTRA TURRAX® type mixer for 5 minutes, after which a 3.5 wt % ethanol 96.5% was dissolved in said mixture under stirring for 5 minutes using a magnetic stirrer. Thereafter, was either 4 wt % Emulfree® or 4 wt % gelling agent (batch F16U248) added to the mixture under stirring for 10 minutes using a magnet stirrer, thereby providing an oleogel.

The oleogel was thereafter added to the aqueous gel under quick stirring using an ULTRA TURRAX® type mixer at 13500 rpm for 10 minutes, and the thereby obtained bigel is then transferred to a mortar.

In order to adjust the pH-value of the bigel, two pH-adjusting solutions, Sol A and Sol B, were prepared.

Sol A: 0.25 wt % sodium methylparaben was dissolved in 3.30 wt % purified water under magnetic stirring.

Sol B: 0.20 wt % sodium hydroxide was dissolved in 1.80 wt % purified water under magnetic stirring.

In order to pH-adjust (neutralize) the bigel; Sol A was first added to the bigel under mixing, and then was Sol B added under mixing.

The physical parameters of the two obtained bigels, one prepared using the Emulfree® P and one prepared using the gelling agent (batch F16U248) according to the invention, are compared in table 4 below.

TABLE 4

| Tests | 1% testo-bigel with Emulfree ® P | 1% testo-bigel with gelling agent |
| --- | --- | --- |
| Visual aspect | White bigel, cream | White bigel, cream |
| Final pH | 4.90 | 4.95 |
| Density | 0.97 | 0.96 |
| Viscosity | 120600 mPa · s | 131600 mPa · s |

The viscosity was measured using a VRM-08 LAMY viscosimeter equipped with a MS DIN 1.3 module. The speed was fixed at 5 rpm (shear rate of 0.8 $s^{-1}$) and the temperature was fixed at 23° C. Time: 30 s.

As is evident from said table, both gels have substantially identical physical characteristics, and the gelling agent obtained using the method according to the invention, is therefore a suitable alternative to the conventional Emulfree®. P composition.

Experiment D: In Vitro Dissolution Test of the 1 wt % Testo-Bigel Obtained in Experiment C In vitro dissolution was assessed using a conventional dissolution test for 8 hours.

Table 5 presents the results of the in vitro dissolution of 1% testo-bigel with Emulfree® P, and table 6 presents the results of the in vitro dissolution of the 1% testo-bigel with the gelling agent according to the invention.

TABLE 5

1% testo-bigel with Emulfree ® P

| | Dissolution Time point (h) | | | | | |
| --- | --- | --- | --- | --- | --- | --- |
| | 0 | 0.5 | 1 | 2 | 4 | 6 | 8 |
| Dissolved % | 0 | 6.3 | 12.1 | 21.7 | 34.5 | 43.7 | 49.5 |
| SD | 0 | 1.8 | 1.8 | 2.8 | 2.7 | 2.1 | 1.3 |
| RSD | 0 | 28.4 | 14.7 | 12.7 | 7.9 | 4.8 | 2.7 |

TABLE 6

1% testo-bigel with gelling agent according to the invention

| | Dissolution Time point (h) | | | | | |
| --- | --- | --- | --- | --- | --- | --- |
| | 0 | 0.5 | 1 | 2 | 4 | 6 | 8 |
| Dissolved % | 0 | 7.9 | 14.1 | 24.6 | 36.8 | 45.4 | 50.2 |
| SD | 0 | 0.9 | 0.9 | 0.9 | 1.5 | 1.7 | 2.2 |
| RSD | 0 | 11.3 | 6.7 | 3.5 | 4.2 | 3.8 | 4.3 |

As is evident from table 5 and 6, the dissolution of the testosterone form both bigels are substantially identical, thus the gelling agent obtained using the method according to the invention did not negatively effect the dissolution of the API, testosterone.

Experiment E: Manufacturing a Gelling Agent (Gelling Agent A) According to the Invention at a Larger Scale Gelling agent A was manufactured as described in experiment A, using the following quantities:
Propyleneglycol laurate: 450 g=90 wt %
Propyleneglycol isostearate: 26.25 g=5.25 wt %
Ethylcellulose: 23.75 g=4.75 wt %

Complete dissolution of the ethylcellulose in the propyleneglycol laurate/propyleneglycol isostearate mixture occurred after about 1 hours.

Gelling agent A had the following parameters:
pH-value: 6.6,
Density: 0.90
Viscosity: 429 mPa·s Viscosity was measured using a VRM-08 LAMY viscosimeter equipped with a MS DIN 1-2 module. The speed was fixed at 50 rpm (share rate of 17.73 s-1) and the temperature was fixed at 46° C. Time up to stabilization.

It can be concluded that the gelling agent A, is substantially similar to batch F16U248 prepared in experiment A, thus it is possible to scale up the production of said gelling agent.

Experiment F: Manufacturing a Bigel (Bigel A) Containing 1 wt % Testosterone at a Greater Scale Bigel A was prepared using gelling agent A obtained in experiment E, and was manufactures as follows:

An aqueous gel was prepared by first heating 1485.88 g (65.45 wt %) purified water to 50° C., and then dissolving 2.3 g (0.10 wt %) sorbic acid in said water, under stirring at 1000 rpm for 15 minutes using a TRIMIX® type mixer. The thereby obtain mixture was then cooled to 25° C., hereafter 32.28 g (1.40 wt %) Carbomer CARBOPOL® 980 NF were dispersed in said mixture under stirring from 1600 to 3000 rpm using a TRIMIX® type mixer, thereby providing the aqueous gel.

The oleogel was prepared by dispersing 23.05 g (1 wt %) testosterone in 461.10 g (20 wt %) Caprylic/Capric triglycerides LABRAFAC CC® under stirring at 8000 rpm using an ULTRA TURRAX® type mixer for 5 minutes, after which 80.69 g (3.5 wt %) ethanol 96.5%, was dissolved in said mixture under stirring at 500 rpm for 5 minutes using a blade type mixer.

Thereafter, was 92.22 g (4 wt %) gelling agent A added to the mixture under stirring at 1300 rpm for 10 minutes using a blade type mixer, thereby providing an oleogel.

The oleogel was thereafter added to the aqueous gel under quick stirring using an TRIMIX® type mixer (10 litre tank) Rotor/strator speed: 3000 rpm; Anchor blade speed: 9 to 45 rpm. Mixing was stopped after 10 minutes, and the thereby obtained first composition is then transferred to a planetary type blender.

In order to adjust the pH-value of the bigel, two pH-adjusting solutions, Sol A and Sol B, were prepared.

Sol A: 5.76 g (0.25 wt %) % sodium methylparaben was dissolved in 76.08 g (3.30 wt %) purified water under magnetic stirring.

Sol B: 4.61 g (0.20 wt %) sodium hydroxide was dissolved in 41.50 g (1.80 wt %) purified water under magnetic stirring.

In order to pH-adjust (neutralize) the bigel; Sol A was first added to the bigel under mixing using a planetary type blender KENWOOD® speed 1, and then Sol B was added under similar conditions, thereby providing bigel A.

Bigel A had the following parameters:
pH-value: 4.8
Density: 0.95
Viscosity: 118,973 mPa·s Viscosity was measured using a VRM-08 LAMY viscosimeter equipped with a MS DIN 1.3 module. The speed was fixed at 50 rpm (share rate of 0.8 s$^{-1}$) and the temperature was fixed at 23° C. Time 30 seconds.

Experiment G: In Vitro Dissolution Test of Bigel A

In vitro dissolution was assessed using the dissolution test of experiment C.

Table 7 presents the results of the in vitro dissolution of bigel A containing 1% testosterone. A dissolution test of a similar bigel prepared with Emulfree® P was also tested for comparison, said results are shown in table 8.

TABLE 7

Bigel A with 1% testosterone

| | Dissolution Time point (h) | | | | | | |
|---|---|---|---|---|---|---|---|
| | 0 | 0.5 | 1 | 2 | 4 | 6 | 8 |
| Dissolved % | 0 | 1.9 | 3.6 | 5.8 | 9.6 | 13.4 | 17.1 |
| SB | 0 | 0.2 | 0.5 | 0.6 | 0.8 | 1.3 | 1.0 |
| RSD | 0 | 12.0 | 14.8 | 10.7 | 8.5 | 8.8 | 5.6 |

TABLE 8

Conventional bigel prepared with Emulfree ® P containing 1% testosterone

| | Dissolution Time point (h) | | | | | | |
|---|---|---|---|---|---|---|---|
| | 0 | 0.5 | 1 | 2 | 4 | 6 | 8 |
| Dissolved % | 0 | 1.9 | 3.5 | 5.8 | 10.0 | 14.6 | 19.7 |
| SD | 0 | 0.3 | 0.3 | 0.6 | 0.6 | 0.9 | 1.4 |
| RSD | 0 | 17.4 | 8.5 | 9.9 | 5.6 | 5.9 | 7.3 |

As is evident from table 7 and 8, the dissolution of the testosterone form both bigels are substantially identical, thus the gelling agent obtained using the method according to the invention did not negatively effect the dissolution of the API, testosterone.

Modifications and combinations of the above principles and designs are foreseen within the scope of the present invention.

What is claimed is:

1. A method for preparing a gelling agent, said method comprises the following consecutive steps:
   a) mixing propyleneglycol laurate and propyleneglycol isostearate, providing a first mixture,
   b) adding ethylcellulose to the first mixture under stirring, thereby providing a second mixture,
   c) continuously stirring the second mixture until a substantially homogeneous gelling agent is formed, and
   wherein step a), b) and c) are performed at a temperature between about 90° C. and about 110° C., and
   wherein the amount of ethylcellulose added in step b) is between 4 wt % and 5.5 wt % based on the total weight of the gelling agent, and wherein the amount of propyleneglycol isostearate added in step a) is at least 5 wt % and not more than 25 wt %, based on the total weight of the gelling agent.

2. The method according to claim 1, wherein the temperature in step a) and/or b) and/or c) is about 100° C.

3. The method according to claim 1, wherein ethylcellulose in step b) is added stepwise to the mixture obtained in step a).

4. The method according to claim 3, wherein between ⅒ and ⅓ of the ethyl cellulose is added in each step-wise step.

5. The method according to claim 1, wherein step a), b) and c) are performed under constant stirring.

6. The method according to claim 1, wherein the ethylcellulose has a molecular weight of about 160,000 g/mol and/or an ethoxyl substitution degree of between 48.0-49.5%.

7. The method according to claim 1, wherein the amount of ethylcellulose added in step b) is about 4.5 wt %, about 4.75 wt %, or about 5 wt %.

8. The method according to claim 1, wherein the amount of propyleneglycol laurate added in step a) is at least 70 wt % and not more than 90 wt %, based on the total weight of the gelling agent.

* * * * *